(12) United States Patent
Noda et al.

(10) Patent No.: US 9,084,889 B2
(45) Date of Patent: Jul. 21, 2015

(54) COMPACT AND LIGHTWEIGHT GANTRY AND PARTICLE BEAM THERAPY DEVICE USING THE SAME

(71) Applicant: HITACHI, LTD., Tokyo (JP)

(72) Inventors: Fumiaki Noda, Tokyo (JP); Takahiro Yamada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/373,939

(22) PCT Filed: Feb. 20, 2013

(86) PCT No.: PCT/JP2013/054068
§ 371 (c)(1),
(2) Date: Jul. 23, 2014

(87) PCT Pub. No.: WO2013/129194
PCT Pub. Date: Sep. 6, 2013

(65) Prior Publication Data
US 2015/0083927 A1    Mar. 26, 2015

(30) Foreign Application Priority Data

Feb. 29, 2012   (JP) .................................. 2012-042694

(51) Int. Cl.
*A61N 5/00*    (2006.01)
*G21K 5/04*    (2006.01)
*A61N 5/10*    (2006.01)

(52) U.S. Cl.
CPC ............ *A61N 5/1077* (2013.01); *A61N 5/1043* (2013.01); *A61N 5/1048* (2013.01); *A61N 5/1065* (2013.01)

(58) Field of Classification Search
CPC . A61N 5/1048; A61N 5/1065; A61N 5/1042; A61N 5/1043; A61N 5/1067; A61N 5/1081; G21K 5/04; G21K 1/093; H05H 7/04
USPC ............ 250/492.3, 398, 252.1, 336.1, 492.1; 315/503, 507
See application file for complete search history.

(56) References Cited

U.S. PATENT DOCUMENTS 4,870,287 A * 9/1989 Cole et al. .................. 250/492.3
5,986,274 A * 11/1999 Akiyama et al. ............ 250/492.3
(Continued)

FOREIGN PATENT DOCUMENTS

JP    10-282300 A    10/1998
JP    11-142600 A    5/1999
(Continued)

OTHER PUBLICATIONS

Spiller et al., "Gantry Studies for the Proposed Heavy Ion Cancer Therapy Facility in Heidelberg", Proceedings of EPAC 2000, pp. 2551-2553, Vienna, Austria.

*Primary Examiner* — David A Vanore
(74) *Attorney, Agent, or Firm* — Mattingly & Malur, PC

(57) ABSTRACT

To provide a preferred device configuration and arrangement capable of forming a large irradiation field, miniaturizing a gantry and reducing weight of the gantry. A gantry includes a bending magnet configured to bend a beam orbit, a plurality of horizontal direction scanning magnets which are first scanning magnets configured to scan the beam orbit in a horizontal direction which is a first direction, and a vertical direction scanning magnet which is a second scanning magnet configured to scan the beam orbit in a vertical direction which is a second direction. The plurality of horizontal direction scanning magnets is arranged so that $\theta$ is equal to or less than 90° when it is assumed that a phase difference between the horizontal direction scanning magnets is $180n°\pm\theta$. The bending magnet is arranged between the plurality of horizontal direction scanning magnets.

8 Claims, 10 Drawing Sheets

(56) References Cited

U.S. PATENT DOCUMENTS

| | | |
|---|---|---|
| 6,034,377 A | 3/2000 | Pu |
| 6,774,383 B2 * | 8/2004 | Norimine et al. .......... 250/505.1 |
| 6,792,078 B2 * | 9/2004 | Kato et al. .................... 378/152 |
| 6,819,743 B2 * | 11/2004 | Kato et al. .................... 378/147 |
| 6,823,045 B2 * | 11/2004 | Kato et al. .................... 378/152 |
| 6,936,832 B2 * | 8/2005 | Norimine et al. .......... 250/505.1 |
| 7,060,997 B2 * | 6/2006 | Norimine et al. .......... 250/505.1 |
| 2005/0247890 A1 * | 11/2005 | Norimine et al. .......... 250/492.3 |
| 2011/0108737 A1 * | 5/2011 | Pu et al. ........................ 250/398 |
| 2012/0238795 A1 * | 9/2012 | Bert et al. ......................... 600/1 |
| 2013/0221213 A1 * | 8/2013 | Takayanagi et al. ....... 250/252.1 |

FOREIGN PATENT DOCUMENTS

| | | |
|---|---|---|
| JP | 2004-121654 A | 4/2004 |
| WO | 2010/140236 A1 | 12/2010 |

\* cited by examiner

COMPACT AND LIGHTWEIGHT GANTRY AND PARTICLE BEAM THERAPY DEVICE USING THE SAME

TECHNICAL FIELD

The present invention relates to a preferred device configuration and arrangement to realize a compact and lightweight gantry for particle beam therapy capable of forming a large irradiation field.

BACKGROUND ART

Recently, as one of cancer treatments, a minimally invasive radiation treatment has attracted attention. The treatment applies less load on a human body and can maintain the quality of life at a high level after the treatment. Particularly, a particle beam therapy system using a charged particle beam such as protons or carbon accelerated by an accelerator such as a synchrotron, a cyclotron, or a linear accelerator provides high dose concentration to an affected part and has been expected as a promising system.

In case of irradiating a patient with a beam accelerated by the accelerator, as a unit to realize improvement of the dose concentration to the affected part and reduction of an irradiation dose to vital organs, irradiation using a rotating gantry which can irradiate with a particle beam from an arbitrary direction is effective. In order to achieve the above irradiation, it is necessary to bend charged particles. However, a magnet tends to increase in size so as to bend a high energy proton or heavier ions such as helium and carbon to obtain a desired irradiation field size. Also, demands for enlarging the irradiation available range tend to increase, and this causes a further increase in size of the magnet. Therefore, it is desired to realize a compact and lightweight rotating gantry, with which a large irradiation field can be formed.

CITATION LIST

Patent Literature

PTL 1: JP 2004-121654 A

Non-Patent Literature

NPL 1: "GANTRY STUDIES FOR THE PROPOSED HEAVY ION CANCER THERAPY FACILITY IN HEIDELBERG", Proceedings of EPAC 2000, p 2551-2553, Vienna, Austria

SUMMARY OF INVENTION

Technical Problem

In the case where an irradiation field size is enlarged, a scanning magnet becomes larger, and a radius of rotation of a gantry increases. NPL 1 discloses a technique which can decrease the radius of rotation of the gantry and can suppress an increase in size of the scanning magnet. However, it is unavoidable that a final magnet becomes larger.

A purpose of the present invention is to realize a gantry which can suppress an increase in size of a magnet and can form a large irradiation field.

Solution to Problem

A gantry includes a bending magnet configured to bend a beam orbit, a plurality of first scanning magnets configured to scan the beam orbit in a first direction, and a second scanning magnet configured to scan the beam orbit in a second direction. The first scanning magnets are arranged at positions where $\theta$ is equal to or less than 90° when it is assumed that a phase difference is $180n°\pm\theta$ (n is a natural number). The bending magnet is arranged between the plurality of first scanning magnets.

Advantageous Effects of Invention

According to the present invention, a gantry which can suppress an increase in size of a magnet and can form a large irradiation field can be realized.

DESCRIPTION OF EMBODIMENTS

Figure 3:
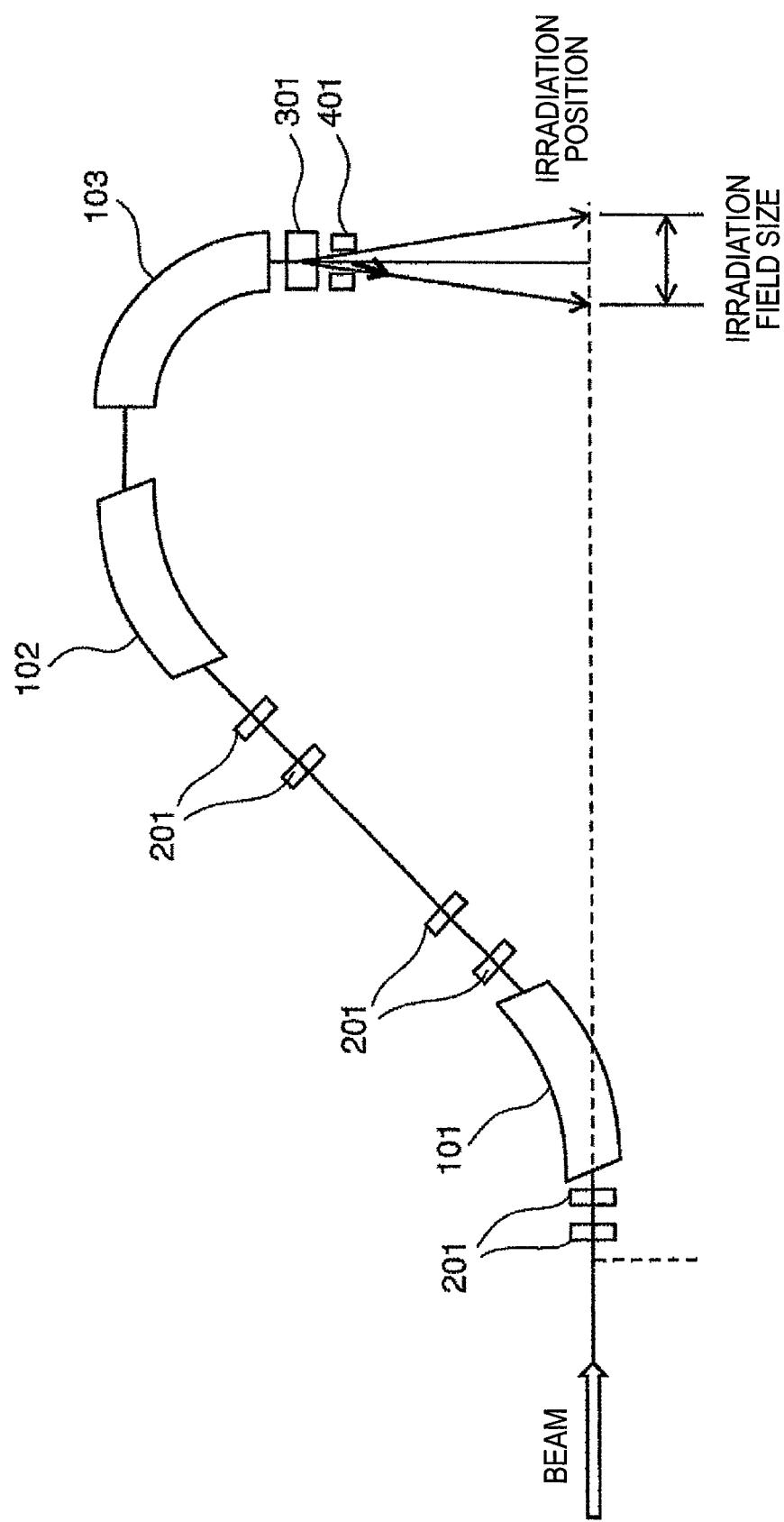
FIG. 3 is a diagram of a configuration of a gantry of Comparative Example 1.

A rotating gantry of Comparative Example 1 which scans and irradiates a beam orbit is shown in FIG. 3. An irradiation gantry includes bending magnets 101, 102, and 103 which bend the beam orbit, a quadrupole magnet 201 which focus/defocus a beam, a horizontal direction scanning magnet 301 which scans with the beam in a horizontal direction, a vertical direction scanning magnet 401 which scans with the beam in a vertical direction. The scanning magnets 301 and 401 are arranged downstream of the final bending magnet 103. The scanning magnets 301 and 401 scan an affected part with the beam (to temporally change a magnetic field of the scanning magnet so as to change an irradiation position of the beam). In this case, when the affected part is irradiated with a high energy proton or heavier ions such as helium and carbon, or when an irradiation field size (dimension of an area capable of being scanned with the beam) increases, it is necessary to increase magnetic field intensities of the scanning magnets 301 and 401 or to lengthen a distance between the scanning magnets and the irradiation position. However, there is a limit to increasing a deflection angle by the scanning magnet which scans with the beam at high speed. Also, when a distance between the scanning magnet and the irradiation position becomes longer, a radius of rotation of the gantry becomes larger.

Figure 4:
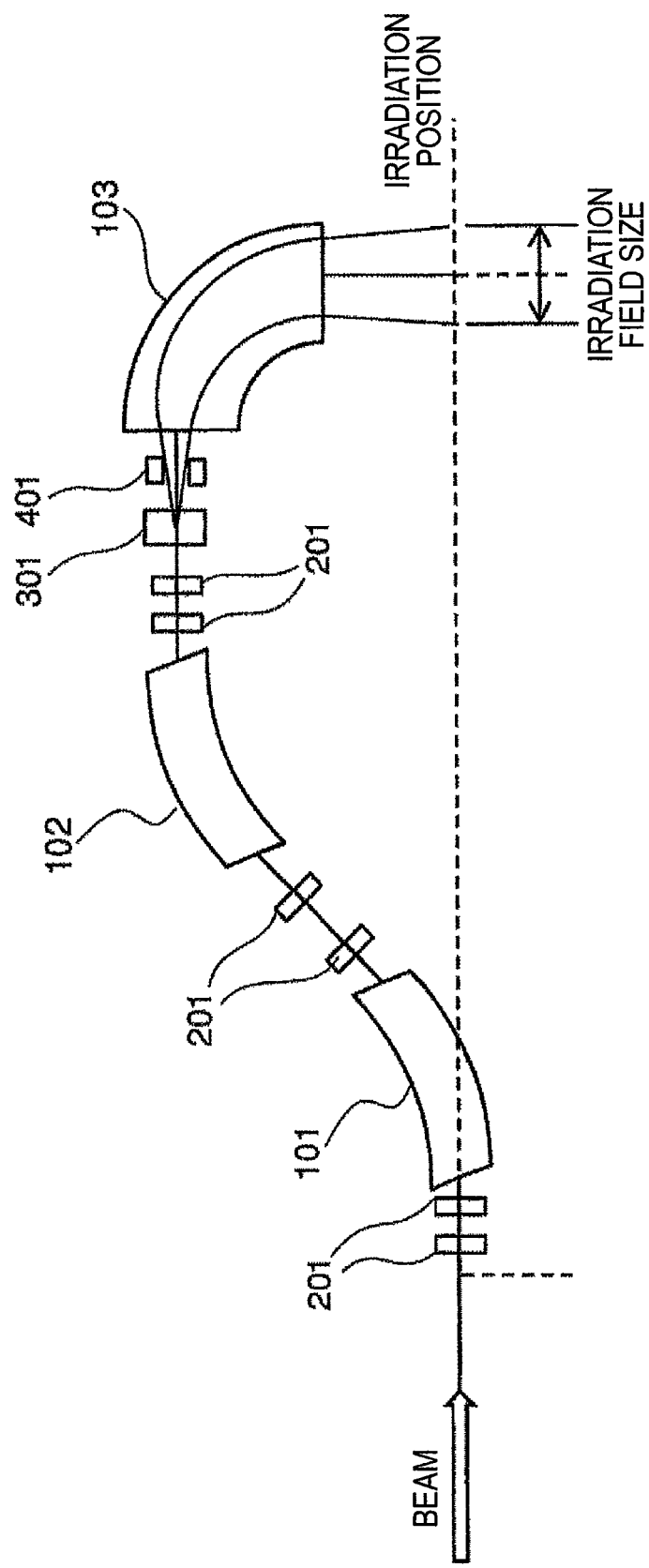
FIG. 4 is a diagram of a configuration of a gantry of Comparative Example 2.

As an idea to solve these problems, NPL 1 discloses an example in which the scanning magnets 301 and 401 are placed upstream of the final bending magnet 103. A device arrangement of the gantry disclosed in NPL 1 is shown as Comparative Example 2 in FIG. 4. In this case, a distance between the scanning magnets 301 and 401 and a point to be irradiated can be secured, and the deflection angles of the scanning magnets can be decreased. Also, the radius of rotation of the gantry can be reduced. On the other hand, the beam is bent by the scanning magnets 301 in the upstream of the final bending magnet 103. Therefore, the beam orbit is displaced in a region of the final bending magnet 103. That is, it is necessary to generate a magnetic field in a large region by the bending magnet 103. As a result, the magnet increases in size. An embodiment of realizing a compact and lightweight gantry which can form a large irradiation field and suppress an increase in size of a magnet will be described below.

Figure 1:
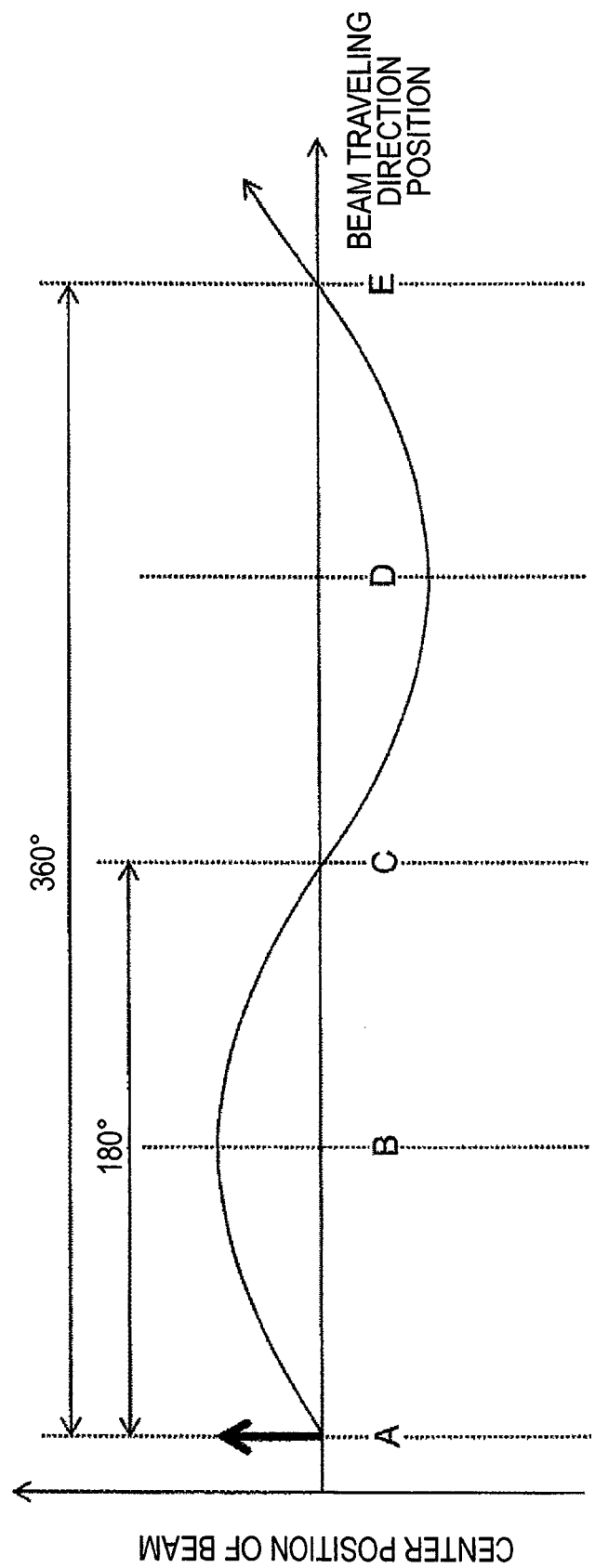
FIG. 1 is a diagram of beam oscillation.
Figure 2:
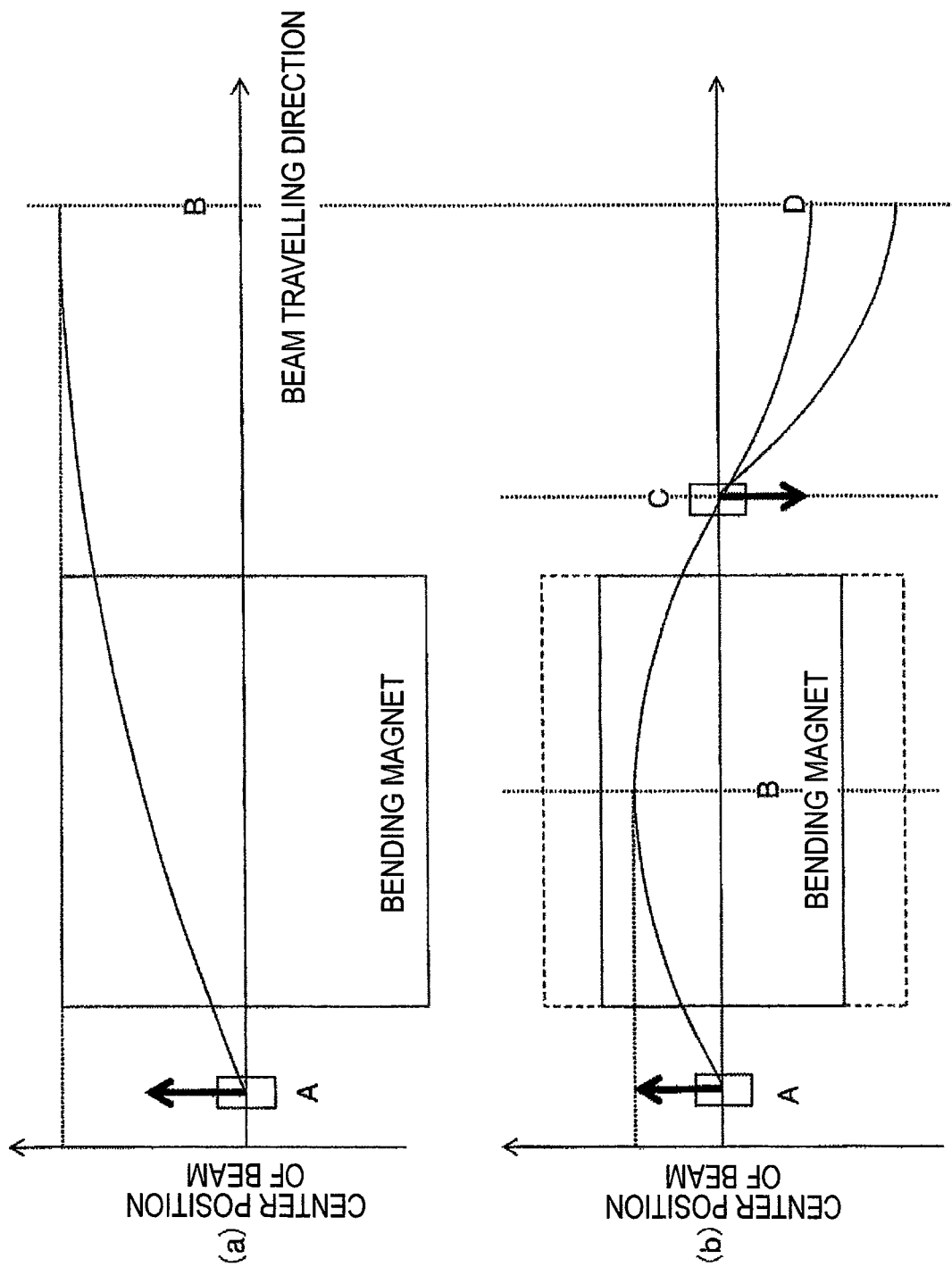
FIGS. 2(a) and 2(b) are diagrams in which a characteristic of the present invention is compared with a related art.

Before starting a specific description of the embodiment, irradiation field formation in each embodiment will be described with reference to FIG. 1 and FIGS. 2(*a*) and 2(*b*). First, in general terms, in a beam optics including a quadrupole magnet (including a magnet which has a quadrupole magnetic field component), a beam orbit change in a case where the magnetic field (bending magnetic field) is applied to the beam at a certain point such that the beam is deviated from a central orbit will be described with reference to FIG. 1. In a case where the beam is bent at a point A, the beam orbit is subjected to a maximum displacement at a point B as shown in FIG. 1. Subsequently, the displacement becomes smaller, and the displacement temporarily becomes 0 at a point C. Subsequently, the beam displacement becomes larger again in the opposite direction. At a point D, the beam displacement becomes the largest and has an opposite sign to that of the point B, and the beam displacement returns to 0 at a point E. Since a beam displacement amount oscillates in this way, the beam displacement amount may be expressed by a phase in which one cycle is 360 degrees.

Next, a case where the irradiation field of a particle beam therapy is formed will be described with reference to FIGS. 2(*a*) and 2(*b*). In Comparative Example 2 of the rotating gantry shown in FIG. 4, an optics is designed such that the point to be irradiated (a position of a patient) is close to the point B in FIG. 1. That is, the optics is designed to scan with the beam at the point A and to have the maximum displacement at the point to be irradiated as shown in FIG. 2(*a*). On the other hand, the scanning magnet is divided into two scanning magnets of the same direction (horizontal or vertical direction) in each embodiment as shown in FIG. 2(*b*). A second scanning magnet is arranged at the point C (a position having a phase of 180° relative to the point A as a reference). A bending direction of the second scanning magnet (downstream-side scanning magnet) is an opposite direction relative to a bending direction of a first scanning magnet (upstream-side scanning magnet). This allows the beam displacement to become the largest at the point D. The beam displacement amount is expressed by a superposition of the displacements by the first and second scanning magnets.

According to each embodiment, since the beam displacement at the point to be irradiated (near the point D) is the superposition of the displacements by the first and second scanning magnets, a necessary bending amount of the first scanning magnet to obtain the same displacement at the point to be irradiated can be reduced. This means that a beam orbit displacement can be reduced in a bending magnet part placed between the first and second scanning magnets. That is, the size and weight of the bending magnet placed between the first and second scanning magnets can be reduced. Therefore, a compact and lightweight gantry can be provided. In other words, when a magnet having the same size as those in Comparative Examples is used, the irradiation field size can be larger than those of Comparative Examples.

First Embodiment

A configuration of a gantry for particle beam therapy according to a first embodiment of the present invention will be described below with reference to FIG. 5.

A particle beam irradiation gantry includes bending magnets 101 to 103 which bend beams, horizontal direction scanning magnets 301 and 302 which scan beam orbits in a horizontal direction, a vertical direction scanning magnet 401 which scans the beam orbit in a vertical direction, a power supply which excites the respective magnets, and a control system (not shown).

As mentioned above, the particle beam irradiation gantry includes two horizontal direction scanning magnets. The upstream-side horizontal direction scanning magnet 301 and the downstream-side horizontal direction scanning magnet 302 are arranged at positions where a phase difference therebetween becomes 180°. A bending direction of the downstream-side horizontal direction scanning magnet 302 is an opposite direction relative to a bending direction of the upstream-side horizontal direction scanning magnet 301. In this case, the beam displacement at the irradiation position is the superposition of the displacements by the scanning magnets 301 and 302. Also, since the beam displacement of the downstream-side scanning magnet 302 can be reduced, a size increase of the downstream-side horizontal direction scanning magnet 302 can be avoided.

The bending magnet 103 is arranged between the horizontal direction scanning magnets 301 and 302. As mentioned above, since the displacement at the irradiation position is the superposition of the displacements by the scanning magnets 301 and 302, amounts of the displacement caused by the respective scanning magnets 301 and 302 can be adjusted. When it is assumed that the displacement amount is ½ of that of Comparative Example 2 including a single scanning magnet, a deflection angle of the upstream-side horizontal direction scanning magnet 301 can be suppressed to about half. This means that the orbit displacement in a region of the bending magnet 103 can be suppressed to about half of Comparative Example. This enables the bending magnet 103 to be compact and lightweight. That is, the bending magnet can be compact and lightweight while the necessary irradiation field size is secured.

In other words, when the bending magnet having the same good field region as those in Comparative Examples is used, it will be possible to approximately double the irradiation field size.

The phase difference between the upstream-side horizontal direction scanning magnet 301 and the downstream-side horizontal direction scanning magnet 302 may be adjusted by adjusting an edge angle or n value of a quadrupole magnet 201 or the bending magnet 103 arranged between the scanning magnets 301 and 302 or by adjusting a quadrupole magnetic field component intensity in a case where dipole and quadrupole magnets are combined.

Also, the horizontal direction scanning magnets 301 and 302 are excited in series by the same power supply. Since the scanning magnets 301 and 302 are excited in opposite directions to each other, the horizontal direction scanning magnets 301 and 302 are connected so that currents flowing in coils also flow in opposite directions to each other. This allows a single scanning magnet power supply to achieve a purpose of the present invention, and the magnets can be easily synchronized.

Although a case of beam scan in the horizontal direction has been described in the present embodiment, a similar effect may also be obtained in a case of the beam scan in the vertical direction.

Also, although the rotating gantry has been described in the present embodiment, a fixed gantry has a similar effect.

Second Embodiment

Figure 6:
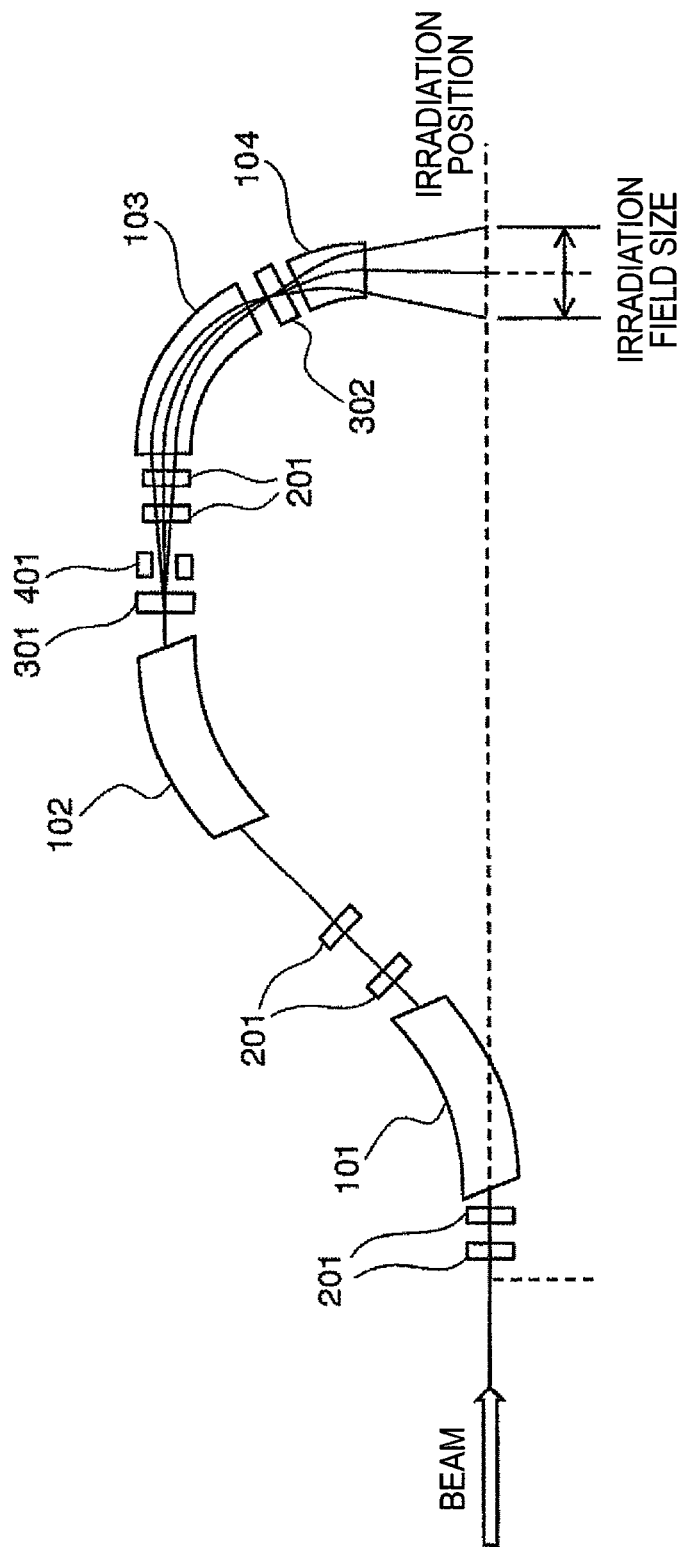
FIG. 6 is a diagram of a configuration of a gantry according to one preferred embodiment (second embodiment) of the present invention.

A configuration of a gantry for particle beam therapy according to a second embodiment of the present invention will be described below with reference to FIG. 6.

A particle beam irradiation gantry includes bending magnets 101 to 104 which bend beams, horizontal direction scanning magnets 301 and 302 which scan beam orbits in a horizontal direction, a vertical direction scanning magnet 401 which scans the beam orbit in a vertical direction, a power supply which excites the respective magnets, and a control system (not shown).

As mentioned above, the particle beam irradiation gantry includes two horizontal direction scanning magnets. The upstream-side horizontal direction scanning magnet 301 and the downstream-side horizontal direction scanning magnet 302 are arranged so that a phase difference therebetween becomes 180°.

The phase difference between the upstream-side horizontal direction scanning magnet 301 and the downstream-side horizontal direction scanning magnet 302 may be adjusted by adjusting an edge angle or n value of a quadrupole magnet 201 or the bending magnet 103 arranged between the scanning magnets 301 and 302 or by adjusting a quadrupole magnetic field component intensity in a case where dipole and quadrupole magnets are combined.

In the second embodiment, the bending magnet 103 mentioned in the first embodiment is divided into a plurality of bending magnets. Here, an example in which the bending magnet is divided into two bending magnets 103 and 104 is shown. The bending magnet 103 is arranged between the horizontal direction scanning magnets 301 and 302. The bending magnet 104 is arranged downstream of the horizontal direction scanning magnet 302. With this arrangement, while a necessary irradiation field size is secured, the bending magnet can be compact and lightweight similarly to the first embodiment. At the same time, a distance between an outlet of the final bending magnet 104 and a point to be irradiated can be shortened, and a radius of rotation of the gantry can be reduced.

Also, the horizontal direction scanning magnets 301 and 302 are excited in series by the same power supply. Since the scanning magnets 301 and 302 are excited in opposite directions to each other, the horizontal direction scanning magnets 301 and 302 are connected so that currents flowing in coils also flow in opposite directions to each other. This allows a single scanning magnet power supply to achieve a purpose of the present invention, and the magnets can be easily synchronized.

Although a case of beam scan in the horizontal direction has been described in the present embodiment, an effect of the present invention can also be obtained similarly in a case of the beam scan in the vertical direction.

Also, although a rotating gantry has been described in the present embodiment, a fixed gantry has a similar effect.

Third Embodiment

Figure 7:
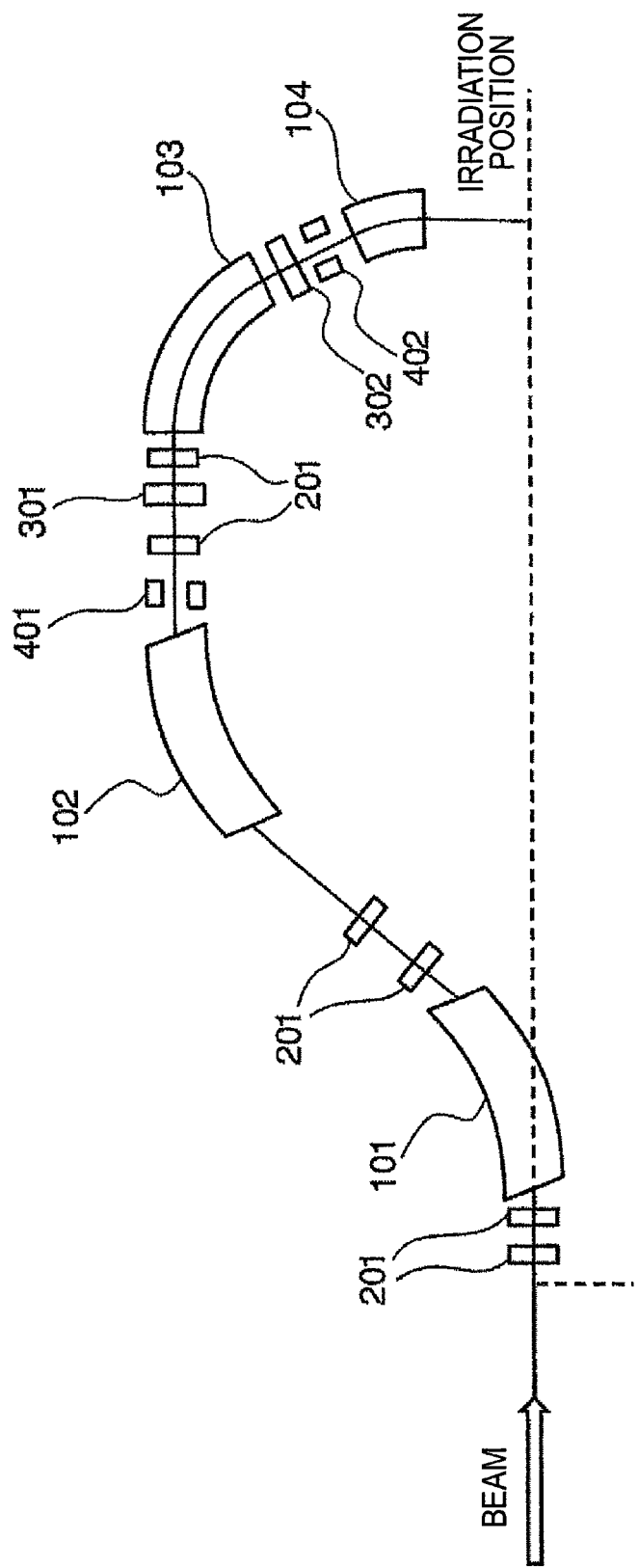
FIG. 7 is a diagram of a configuration of a gantry according to one preferred embodiment (third embodiment) of the present invention.

A configuration of a gantry for particle beam therapy according to a third embodiment of the present invention will be described below with reference to FIG. 7.

A particle beam irradiation gantry includes bending magnets 101 to 104 which bend beams, horizontal direction scanning magnets 301 and 302 which scan beam orbits in a horizontal direction, vertical direction scanning magnets 401 and 402, a power supply which excites the respective magnets, and a control system (not shown).

The particle beam irradiation gantry includes two horizontal direction scanning magnets and two vertical direction scanning magnets. The respective scanning magnets are arranged so that a phase difference between the upstream-side horizontal direction scanning magnet 301 and the downstream-side horizontal direction scanning magnet 302 becomes 180° and a phase difference between the upstream-side vertical direction scanning magnet 401 and the downstream-side vertical direction scanning magnet 402 also becomes 180°.

At this time, by arranging the downstream-side horizontal direction scanning magnet 302 adjacent to the downstream-side vertical direction scanning magnet 402, beam displacement amounts at positions of the downstream-side scanning magnets 302 and 402 can be reduced. This arrangement can suppress an increase in a pole width and a gap width of the downstream-side scanning magnets.

The phase difference between the scanning magnets may be adjusted by adjusting an edge angle or n value of a quadrupole magnet 201 or the bending magnet 103 arranged between the scanning magnets or by adjusting a quadrupole magnetic field component intensity in a case where dipole and quadrupole magnets are combined.

Also, the horizontal direction scanning magnets 301 and 302, and the vertical direction scanning magnets 401 and 402 are respectively excited in series by the same power supply. The scanning magnets 301 and 302 bend the beams in opposite directions to each other, and the scanning magnets 401 and 402 bend the beams in opposite directions to each other. Therefore, the respective pairs of scanning magnets are arranged so that currents flowing in coils also flow in opposite directions to each other. This allows a single horizontal scanning magnet power supply and a single vertical scanning magnet power supply to achieve a purpose of the present invention, and the magnets can be easily synchronized.

Also, although a rotating gantry has been described in the present embodiment, a fixed gantry has a similar effect.

The gantry described above according to each embodiment includes the bending magnet 103 which bends the beam orbit, the horizontal direction scanning magnets 301 and 302 which are first scanning magnets for scanning the beam orbit in the horizontal direction which is a first direction, the vertical direction scanning magnet 401 which is a second scanning magnet for scanning the beam orbit in the vertical direction which is a second direction. The gantry includes the plurality of horizontal direction scanning magnets 301 and 302. The horizontal direction scanning magnets 301 and 302 are arranged so that the phase difference between the horizontal direction scanning magnets 301 and 302 becomes a natural number multiple of 180°. The bending magnet 103 is arranged between the plurality of horizontal direction scanning magnets 301 and 302. With this configuration, by using the superposition of the beam displacement by the plurality of first scanning magnets, the gantry which can form a large irradiation field while suppressing the increase in size of the magnet can be realized.

Here, in the description, it is assumed that the first direction is the horizontal direction and the second direction is the vertical direction. However, the directions may be reversed to obtain a similar effect. The plurality of second scanning magnets is included in addition to the first scanning magnets, and the second scanning magnets are arranged at positions where the phase difference therebetween becomes a natural number multiple of 180°. The bending magnet 103 is arranged between the plurality of second scanning magnets. This can further enhance the effects in which the increase in size of the magnet can be suppressed and the large irradiation field can be obtained.

At this time, when the horizontal direction scanning magnet 302 and the vertical direction scanning magnet 402, which are respectively the first scanning magnet and the second scanning magnet on the downstream side in the beam orbit, are arranged adjacent to each other, the beam displacement amounts at these magnet positions can be reduced, and the increase in size of the magnet can be suppressed. Here, "adjacent" means an arrangement in which another magnet does not exist between the horizontal direction scanning magnet 302 and the vertical direction scanning magnet 402.

In addition to the bending magnet 103 arranged between the plurality of first scanning magnets, the bending magnet 104 which is a second bending magnet is included on the downstream side of the horizontal scanning magnet 302 or the vertical scanning magnet 402 which is the first scanning magnet on the downstream side in the beam orbit. This can shorten a distance between the bending magnet 104 and an object to be irradiated so that the radius of rotation of the gantry can be reduced and the gantry can be miniaturized.

Figure 8:
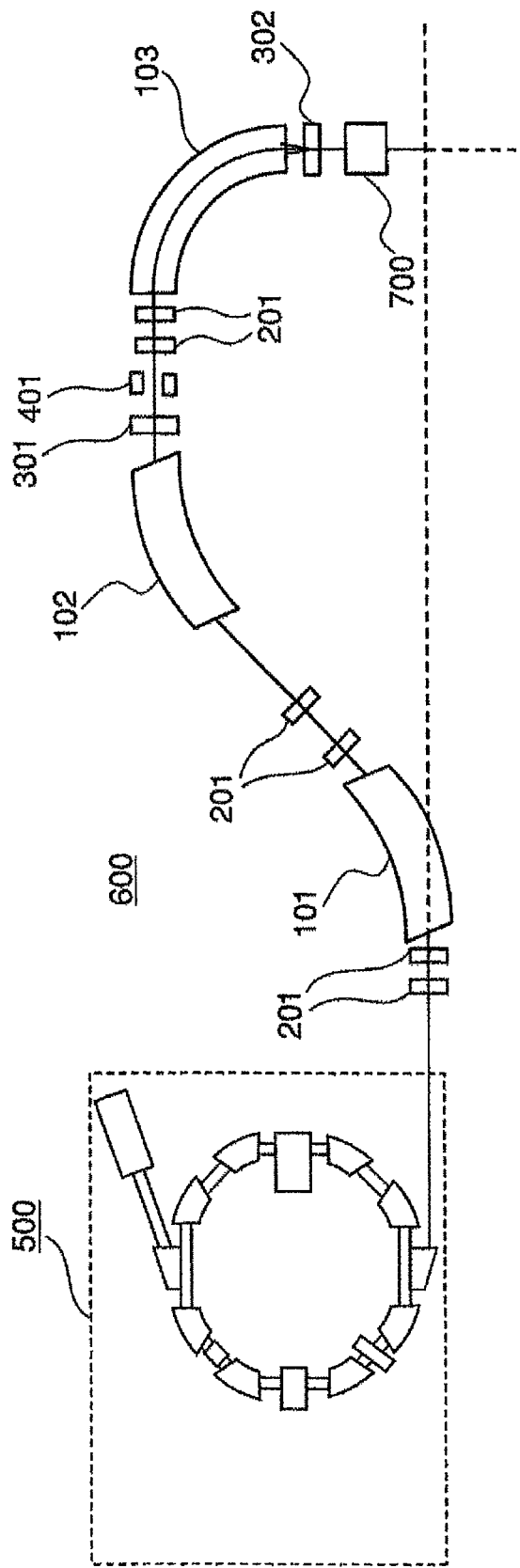
FIG. 8 is a diagram of a particle beam therapy system.

As shown in FIG. 8, the gantry described in each embodiment is used as a part of a transport unit of a particle beam therapy device. The particle beam therapy device includes an accelerator 500 which accelerates the beam, an irradiation device 700 which irradiates with the beam, and a transport unit 600 which transports the beam which has been accelerated by the accelerator to the irradiation device. The whole particle beam therapy device can be miniaturized and the cost can be reduced by using the gantry according to each embodiment.

A control device of the particle beam therapy device can perform control such that the first scanning magnets 301 and 401 on the upstream side in the beam orbit and the first scanning magnets 302 and 402 on the downstream side in the beam orbit respectively have opposite bending directions to each other. The beam displacements of the first scanning magnets can be superposed by this control.

When the first scanning magnets arranged on the upstream side and the downstream side of the bending magnet 103 of the particle beam therapy device are connected to the same power supply so that currents flowing in coils flow in opposite directions to each other, it is not necessary to provide individual power supplies to the respective scanning magnets. Also, the magnets can be easily synchronized.

In each embodiment, it is assumed that the phase difference between the two scanning magnets 301 and 302 becomes a natural number multiple of 180°. However, even in a case where the phase difference is different in some degree from a natural number multiple of 180°, that is, in a case where it is assumed that the phase difference is 180n°±θ and θ is not 0, a similar effect can be obtained (it is assumed that n is a natural number and θ is equal to or more than 0). This point will be described with reference to FIGS. 9(a) to 9(e) and FIGS. 10(a) and 10(b).

Figure 9:
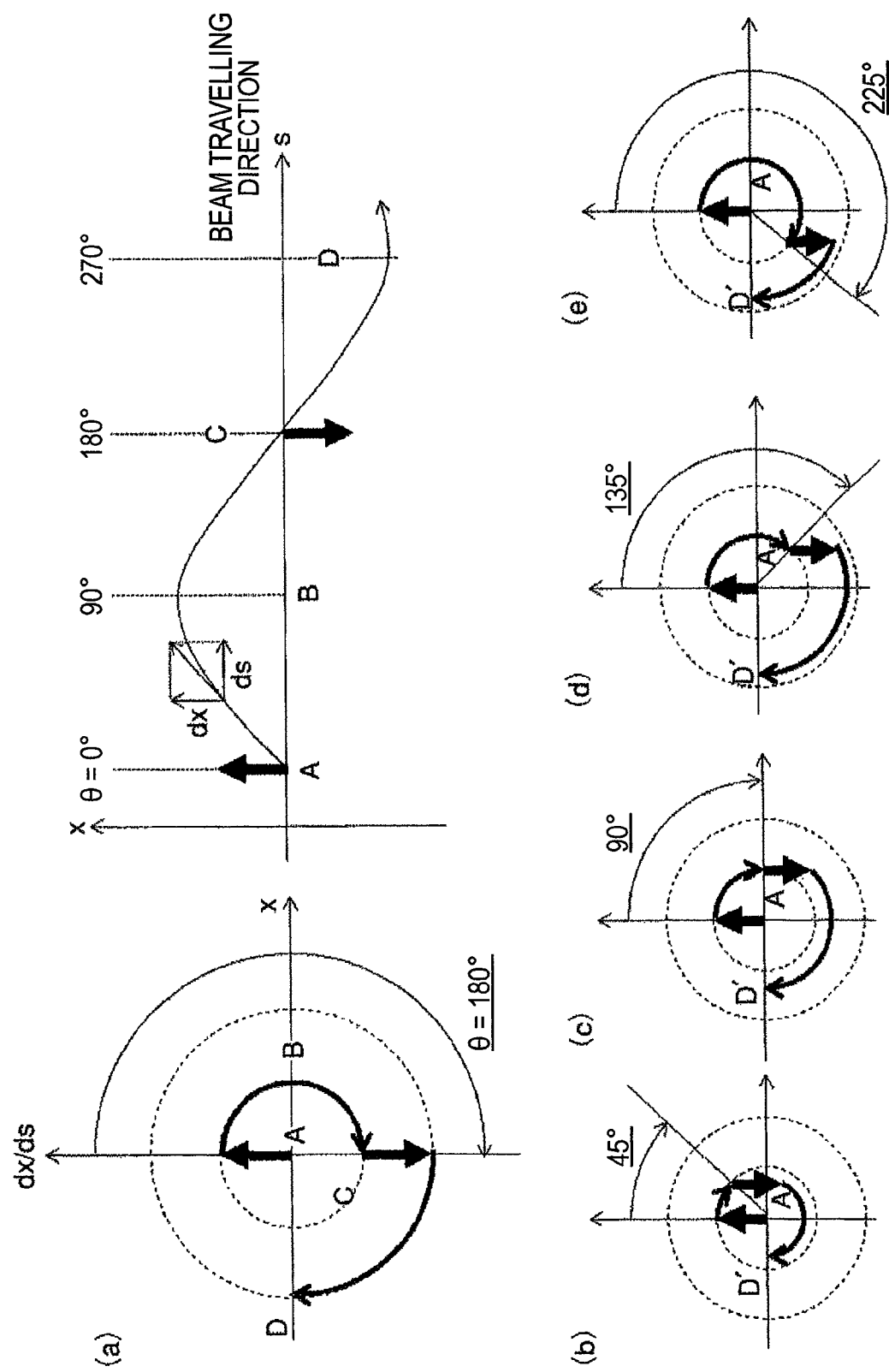
FIGS. 9(a) to 9(e) are diagrams of a relationship between a phase difference and an orbit displacement between scanning magnets.

FIGS. 9(a) to 9(e) and FIGS. 10(a) and 10(b) are diagrams of relationships between θ and an orbit displacement x in a case where it is assumed that the phase difference between the gantry scanning magnets of each embodiment is 180n°±θ. FIG. 9(a) is a diagram in which beam oscillation is simplified by a simple harmonic oscillation model and beam positions x at the respective positions A to D and angles dx/ds at the respective points are illustrated on a plane surface x–dx/ds. As shown in FIG. 9(a), each embodiment corresponds to a case where it is assumed that the phase difference between the upstream-side first scanning magnet 301 and the downstream-side first scanning magnet 302 is 180°. In this case, an effect to increase an absolute value of an orbit displacement x at the point D is the largest. FIG. 9(b) is a diagram of a case where the downstream-side scanning magnet 302 is arranged at the position of θ=45° which is the upstream of the point B. In this case, the orbit displacement at a point D' is rather smaller than a case where the upstream-side scanning magnet 301 alone bends the beam. In FIGS. 9(c) to 9(e), the beam displacement at the point D' becomes larger than a case where the upstream-side scanning magnet 301 alone bends the beam. An effect in which the downstream-side scanning magnet 302 bends the beam in an opposite direction relative to the upstream-side scanning magnet 301 can be obtained. In this way, the effect of each embodiment is not limited to the phase difference of 180°. The effects can be obtained in a case where the above-mentioned θ is in a certain range.

Figure 10:
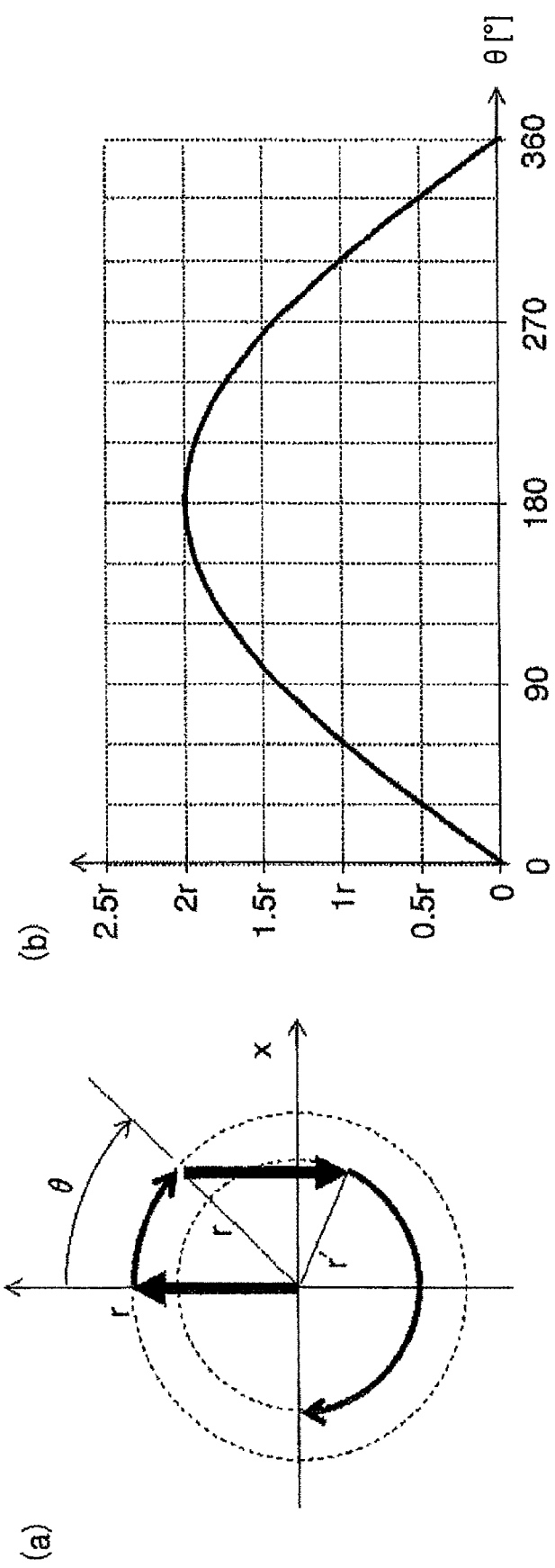
FIGS. 10(a) and 10(b) are diagrams of the relationship between the phase difference and the orbit displacement between the scanning magnets.

A relationship between the above effect and a range of θ will be quantitatively indicated with reference to FIGS. 10(a) and 10(b). Although the actual beam oscillation is not unsophisticated simple harmonic oscillation, in the description here, it is assumed that the actual beam oscillation is the simple harmonic oscillation.

In a case where absolute values of deflection angles of the upstream-side scanning magnet 301 and the downstream-side scanning magnet 302 are the same (both values are represented by r.), a deflection angle r' obtained by synthesizing the deflection angles of the first and second scanning magnets is expressed by formula (1). When plotting the deflection angle r' as a function of θ, it will be expressed by a form shown in FIG. 10(b).

[formula 1]

$$r' = r\sqrt{2(1-\cos\theta)} \quad (1)$$

When a position where the downstream-side horizontal scanning magnet 302 is arranged is a position where a phase from the upstream-side horizontal scanning magnet 301 is 180°±120°, that is, as long as θ is equal to or less than 120°, the above effect can be obtained. However, when θ is 120° or 110°, a little effect can be obtained.

In each embodiment, in order to obtain a maximum effect, in which the increase in size of the magnet can be suppressed and the large irradiation field can be formed, it is preferable that θ be 0 so that a bending effect by the downstream-side scanning magnet 302 becomes 100% (r'=2.0 r). In order to obtain a large bending effect (90%, r'=about 1.9 r) while a factor such as a restriction regarding a placement of each magnet is considered, it is preferable that θ be equal to or less than 45°. In order to obtain a minimum bending effect (50%, r'=about 1.5 r) in spite of having other large restrictions, θ is set equal to or less than 90°. To maintain a balance between the bending effect and other restrictions, it is preferable that the bending effect be set about 75% (r'=1.75 r) and θ be equal to or less than 60°.

The phase difference of 180n°±θ between the horizontal scanning magnets 301 and 302 has been described above. However, it is obvious that a similar description regarding θ can be applied to a phase difference of 180n°±θ between the vertical direction magnets 401 and 402.

The positions of the scanning magnets 301, 302, 401, and 402 have been described in each embodiment, and each position above is a center position of each scanning magnet in a direction along the beam flow.

Figure 5:
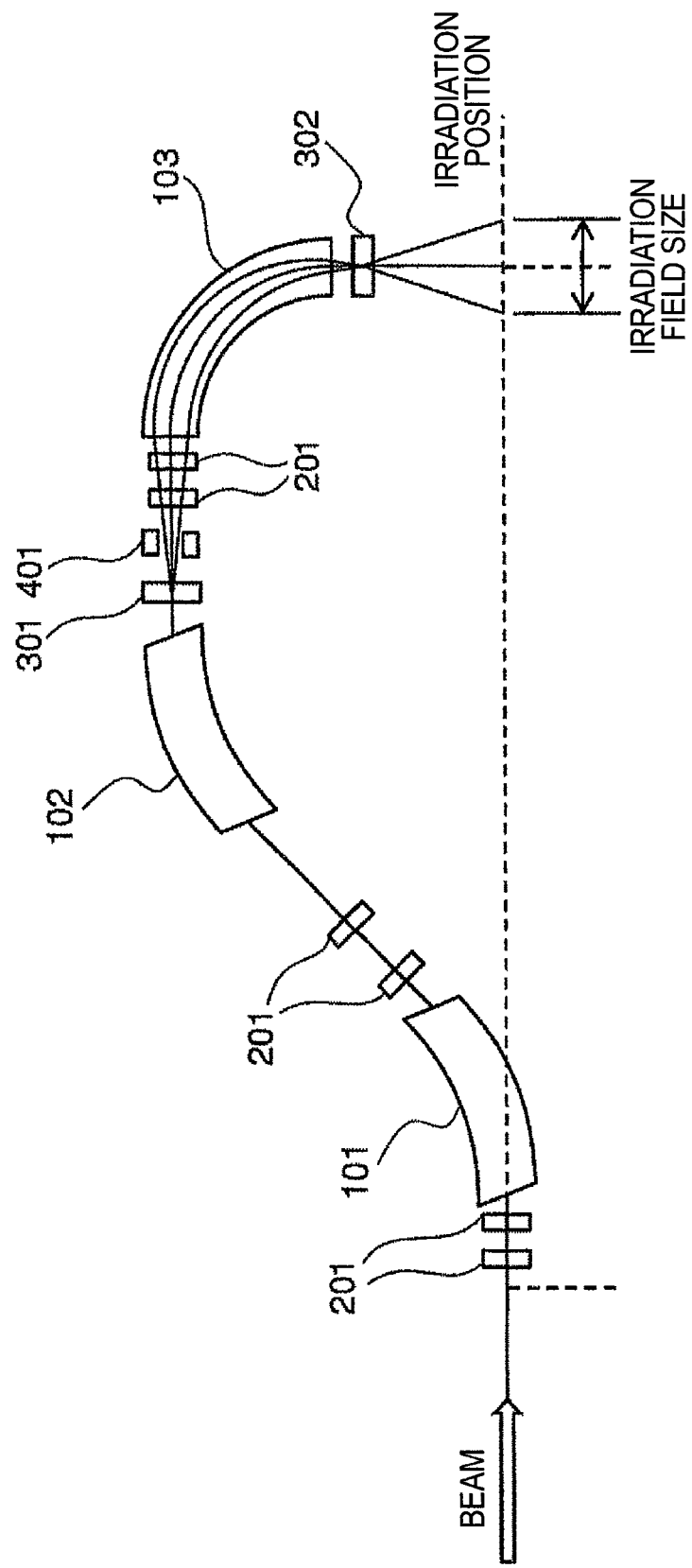
FIG. 5 is a diagram of a configuration of a gantry according to one preferred embodiment (first embodiment) of the present invention.

Finally, a difference between PTL 1 and the first embodiment shown in FIG. 5 will be illustrated for the description of the present invention. First, an outline of the gantry in PTL 1 will be described.

In PTL 1, it is assumed that an example, in which a vertical direction magnet is arranged at a position (the phase is 180° downstream) where a beam bent by a horizontal direction scanning magnet focuses, is a comparison object. PTL 1 discloses the invention for suggesting an improvement to the above example. Specifically, the scanning magnets are arranged, from the upstream side to the downstream side, in the order of the upstream-side horizontal scanning magnet, the bending magnet, the downstream-side horizontal scanning magnet, and the vertical scanning magnet. The scanning magnets are arranged so that the focal point is on the downstream side of the downstream-side horizontal scanning magnet. The vertical scanning magnet is arranged at the focal point. By this arrangement, a function of the downstream-side horizontal scanning magnet can reduce a gap between the beam positions. Therefore, the bending magnet can be miniaturized. Since it is necessary that the focal point be in the downstream of the downstream-side horizontal scanning magnet, it is preferable that a phase difference between the upstream-side horizontal scanning magnet and the downstream-side horizontal scanning magnet be less than 90°. This is because an effect to miniaturize the bending magnet cannot be obtained when the phase difference is equal to or more than 90°.

On the other hand, the upstream-side horizontal scanning magnet 301, the bending magnet 103, and the downstream-side horizontal scanning magnet 302 are arranged in this order in the first embodiment according to the present invention shown in FIG. 5. However, it is preferable that the downstream-side horizontal scanning magnet 302 be near the focal point. Also, to obtain a minimum bending effect (50%, r'=about 1.5 r), it is necessary that θ be equal to or less than 90° when the phase difference is expressed as $180n°±θ$.

In this way, the purpose of PTL 1 is to reduce the gap between the beam positions and to miniaturize the bending magnet. Therefore, it is necessary that θ be less than 90°. On the other hand, it is necessary that θ be equal to or less than 90° so as to use a minimum superposition effect of the beam displacement in each embodiment according to the present invention. In this way, PTL 1 and embodiments according to the present invention are similar in an attention on the arrangement of the scanning magnet. However, ideas and configurations are different between PTL 1 and embodiments according to the present invention.

REFERENCE SIGNS LIST

101 to 104 bending magnet
201 quadrupole magnet
301, 302, 401, 402 scanning magnet
500 accelerator
600 transport unit
700 irradiation device

The invention claimed is:

1. A gantry comprising:
   a bending magnet configured to bend a beam orbit;
   a plurality of first scanning magnets configured to scan the beam orbit in a first direction; and
   a second scanning magnet configured to scan the beam orbit in a second direction, wherein
   the plurality of first scanning magnets is arranged at positions where θ is equal to or less than 90° when it is assumed that a phase difference is 180n°±θ (n is a natural number), and
   the bending magnet is arranged between the plurality of first scanning magnets.

2. The gantry according to claim 1, comprising:
   a plurality of second scanning magnets, wherein
   the plurality of second scanning magnets is arranged at positions where θ is equal to or less than 90° when it is assumed that the phase difference is 180n°±θ (n is a natural number), and
   the bending magnet is arranged between the plurality of second scanning magnets.

3. The gantry according to claim 2, wherein
   the first and second scanning magnets on a downstream side in the beam orbit are adjacent to each other.

4. The gantry according to claim 1, comprising:
   a second bending magnet arranged further downstream of the first scanning magnet on the downstream side in the beam orbit.

5. The gantry according to claim 1, wherein
   θ is equal to or less than 45°.

6. A particle beam therapy device comprising:
   an accelerator configured to accelerate a beam;
   an irradiation device configured to irradiate with the beam; and
   a transport unit configured to transport the beam accelerated by the accelerator to the irradiation device, wherein
   the transport unit includes a gantry including:
      a bending magnet configured to bend a beam orbit;
      a plurality of first scanning magnets configured to scan the beam orbit in a first direction; and
      a second scanning magnet configured to scan the beam orbit in a second direction,
   the plurality of first scanning magnets is arranged at positions where θ is equal to or less than 90° when it is assumed that a phase difference of the plurality of first scanning magnets is 180n°±θ (n is a natural number), and
   the bending magnet is arranged between the plurality of first scanning magnets.

7. The particle beam therapy device according to claim 6, comprising:
   a control device configured to control such that bending directions of the first scanning magnet on an upstream side and the first scanning magnet on a downstream side in the beam orbit are opposite to each other.

8. The particle beam therapy device according to claim 6, wherein
   the first scanning magnets respectively arranged on the upstream side and the downstream side of the bending magnet are connected to a same power supply so that currents flowing in coils flow in opposite directions to each other.

* * * * *